(12) United States Patent
Quarre et al.

(10) Patent No.: US 10,215,169 B2
(45) Date of Patent: Feb. 26, 2019

(54) APPARATUS, SYSTEM, AND METHOD FOR INTRODUCING A LIQUID INTO A VESSEL

(71) Applicant: RareCyte, Inc., Seattle, WA (US)

(72) Inventors: Steve Quarre, Seattle, WA (US); Edward Shafer, Bellevue, WA (US); Lance U'Ren, Seattle, WA (US); Jennifer Chow, Seattle, WA (US)

(73) Assignee: RareCyte, Inc., Seattle, WA (US)

( * ) Notice: Subject to any disclaimer, the term of this patent is extended or adjusted under 35 U.S.C. 154(b) by 89 days.

(21) Appl. No.: 15/595,707

(22) Filed: May 15, 2017

(65) Prior Publication Data

US 2018/0030979 A1 Feb. 1, 2018

Related U.S. Application Data

(60) Provisional application No. 62/367,776, filed on Jul. 28, 2016.

(51) Int. Cl.
| | | |
|---|---|---|
| *F04B 1/12* | (2006.01) |
| *F04B 49/02* | (2006.01) |
| *G01N 30/34* | (2006.01) |
| *F04B 1/28* | (2006.01) |
| *F04B 17/00* | (2006.01) |
| *F04B 17/03* | (2006.01) |
| *F04B 43/12* | (2006.01) |
| *F04B 49/08* | (2006.01) |
| *G01N 30/32* | (2006.01) |
| *G01N 30/02* | (2006.01) |

(52) U.S. Cl.
CPC .............. *F04B 49/022* (2013.01); *F04B 1/28* (2013.01); *F04B 17/003* (2013.01); *F04B 17/03* (2013.01); *F04B 43/12* (2013.01); *F04B 49/08* (2013.01); *G01N 30/34* (2013.01); *F04B 1/12* (2013.01); *G01N 30/02* (2013.01); *G01N 2030/326* (2013.01)

(58) Field of Classification Search
CPC ...... F04B 49/022; F04B 17/03; F04B 17/003; F04B 49/08; F04B 43/12; F04B 1/28; F04B 1/12; G01N 30/34; G01N 2030/326; G01N 30/02
See application file for complete search history.

(56) References Cited

U.S. PATENT DOCUMENTS 6,324,926 B1 * 12/2001 Lehtinen ............ G01N 35/1079
141/330

* cited by examiner

*Primary Examiner* — Jason K Niesz
(74) *Attorney, Agent, or Firm* — Shay Glenn LLP

(57) ABSTRACT

This disclosure is directed to an apparatus, system and method for introducing a liquid into a vessel. A fluid layering system includes a pump connected to a line connected to a connector, such that the connector provides an air-tight fit with the vessel.

20 Claims, 4 Drawing Sheets

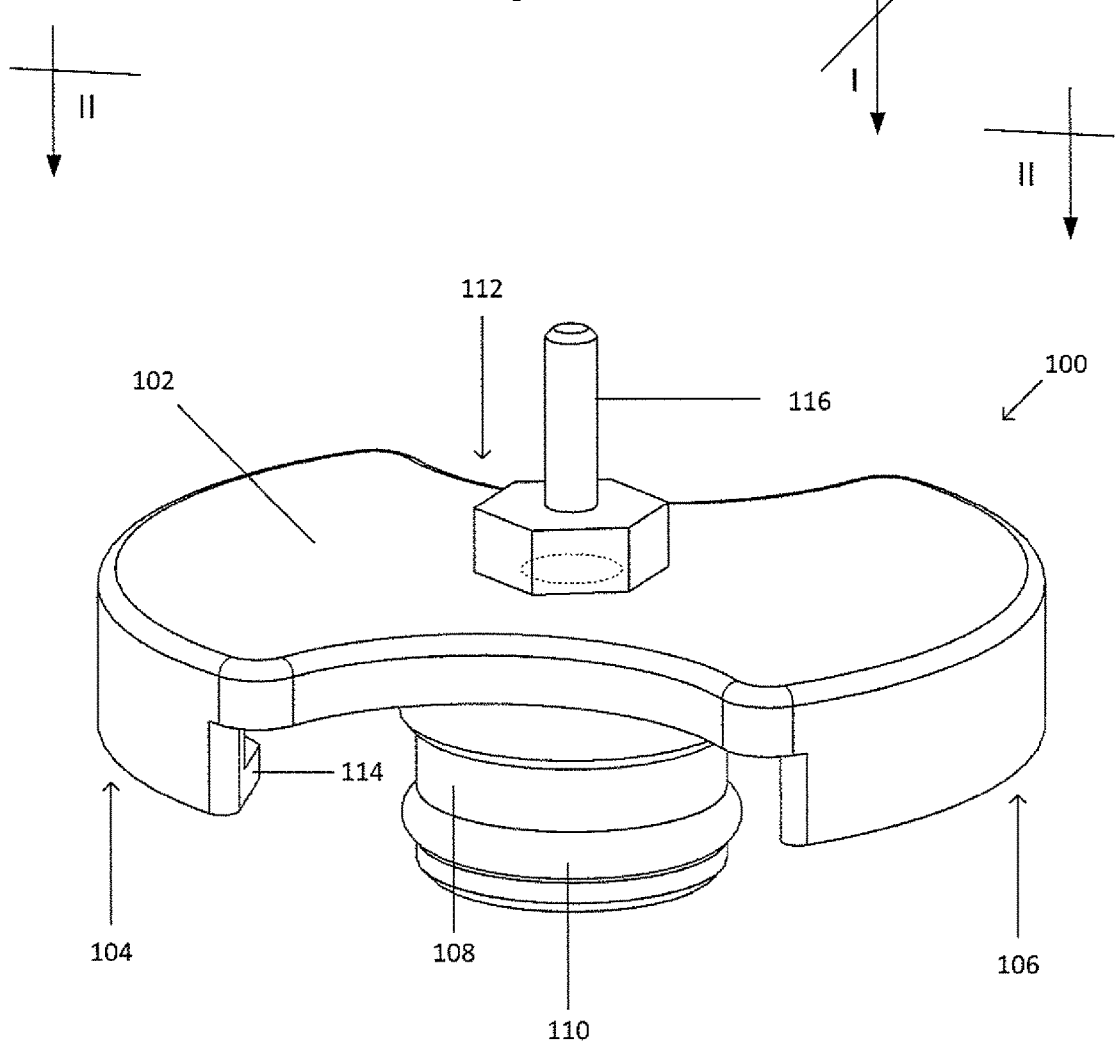

APPARATUS, SYSTEM, AND METHOD FOR INTRODUCING A LIQUID INTO A VESSEL

CROSS-REFERENCE TO A RELATED APPLICATION

This application claims the benefit of Provisional Application No. 62/367,776, filed Jul. 28, 2016.

TECHNICAL FIELD

This disclosure relates generally to a pump and, in particular, to a pump for filling a vessel with a liquid.

BACKGROUND

Generally, a sealed, liquid-containing vessel may include air which may be desirous to remove, such that the remaining volume of the sealed portion of the vessel may be filled with liquid. In doing so, the air within the sealed portion of the fluid-containing vessel is replaced with the liquid. As a result, practitioners, researchers, and those working with liquid-containing vessels continue to seek devices, systems, and methods to accurately fill a sealed vessel with a liquid.

DESCRIPTION OF THE DRAWINGS

FIGS. 1A-1C show an example cap.

DETAILED DESCRIPTION

This disclosure is directed to an apparatus, system and method for introducing a liquid into a vessel. A fluid layering system includes a pump connected to a line connected to a connector, such that the connector provides an air-tight or a fluid-tight fit with the vessel.

In the following description, the term "pressure gradient" is used to describe the difference in pressure between a pump (such as a pump 212, discussed below) and a sealed portion of a vessel (such as a sealed portion 306 of the vessel 304, discussed below).

Figure 1B:
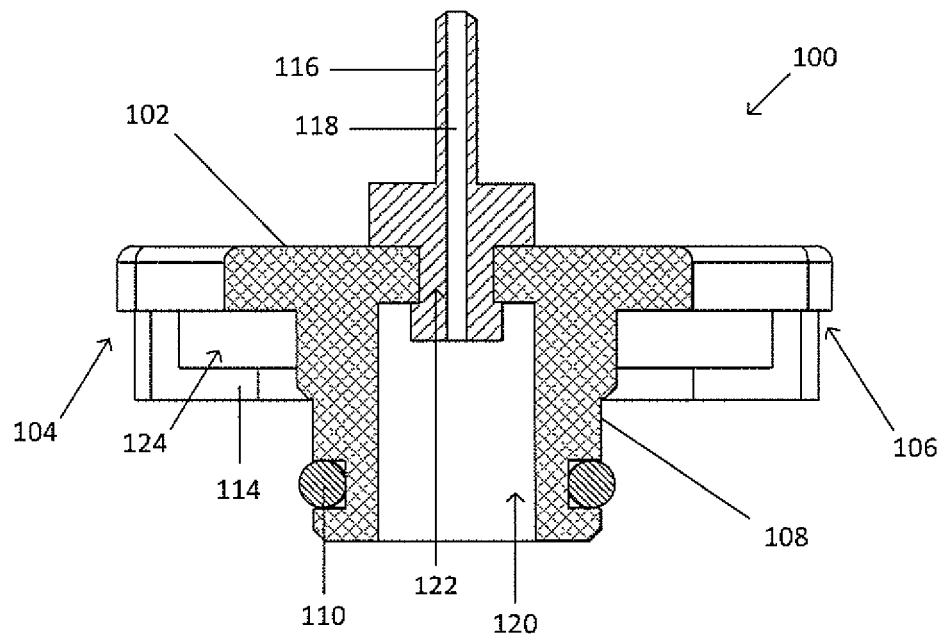
Figure 1C:
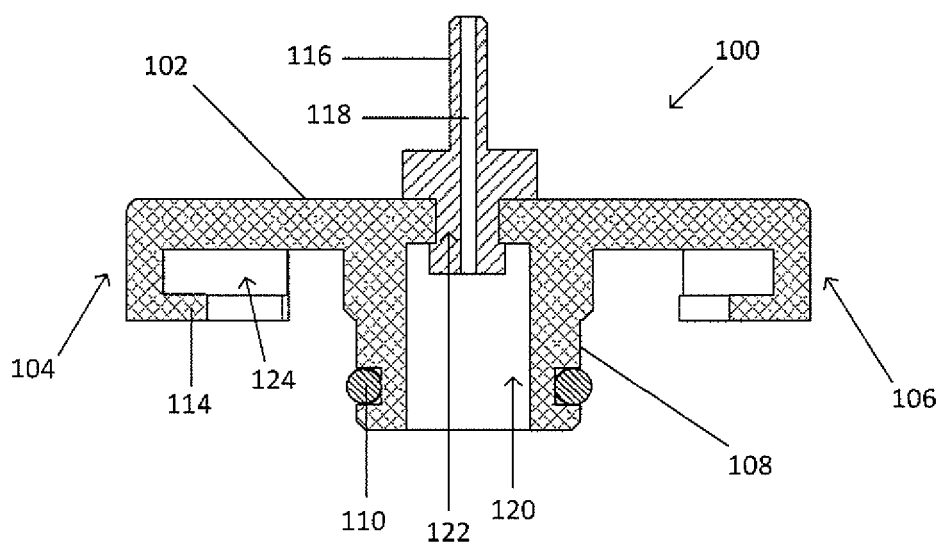

FIG. 1A shows an isometric view of a cap 100. FIG. 1B shows a cross-section of the cap 100 taken along the line I-I. FIG. 1C shows a cross-section of the cap 100 taken along the line II-II. The cap 100 includes a main body 102 with a hole 122 and a shaft 108 extending away from the main body 102, such as in a downward or upward direction. The main body 102 may also include a first end 104 and a second end 106 extending in the same or substantially the same direction as the shaft 108 from the main body. The first and second ends 104, 106 may each include a finger 114 extending towards or substantially towards the shaft 108, thereby also forming a groove 124 located between the main body 102 and the finger 114 of each respective side. The main body 102 may have at least one notch 112 for gripping, holding, and/or rotating purposes. The shaft 108 includes a cavity 120 extending longitudinally and may include a sealing member 110 extending circumferentially around the shaft 108. The cavity 120 and the hole 122 are adjoining and in fluid communication with each other.

The cap 100 may also include a conduit 222 having a first end and second end, such that the conduit 222 is located within the hole 122 and the second end is at least partially located within the cavity 120. The conduit 222 includes a bore 118 extending from the first end to the second end, wherein the bore 118 and the first end of the conduit 222 are in fluid communication with the cavity 120. The conduit 222 and the main body 102 may be separate pieces (i.e. the conduit 222 is inserted into the main body 102) or may be a single piece (i.e. formed within a mold or by machining). The cap 100, and any of its components, may be composed of glass, plastic, metal, or any suitable material.

Figure 2:
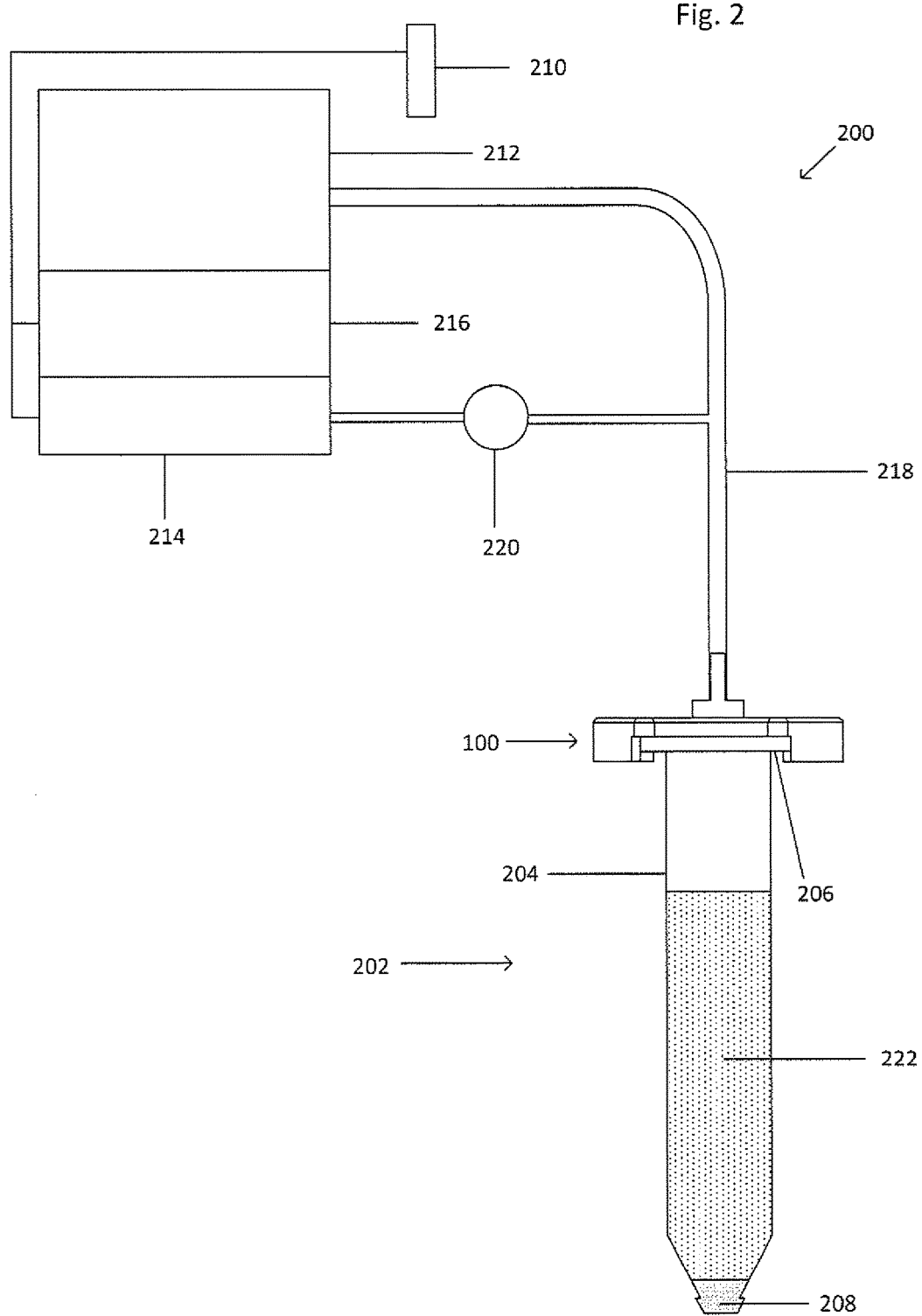
FIG. 2 shows an example fluid layering system.

FIG. 2 shows an example fluid layering system 200. The fluid layering system 200 includes a pump 212, the cap 100, and a hose 218 to fluidly couple the pump 212 to the cap 100. A first end of the hose 218 is connected to the pump 212 and a second end of the hose 218 is connected to the first end of the conduit 222 of the cap 100. The pump 212 may be connected to a motor 216 which may be operated by a controller 214, at least one of which may be activated by a switch 210. Alternatively, the switch 210 may be integrated into the controller 214. Additionally, the fluid layering system 200 may include a pressure sensor 220, connected to the controller 214, to determine the pressure within the tube 218. The pump 212 may be a syringe pump, a piezo pump, a peristaltic pump, or the like. The motor 216 may be a stepper motor, a DC motor, or a servo motor.

The tube 202, which may be an Eppendorf tube, a syringe, or a test tube, includes a main body 204 having a first open end and a second end including a plug 208. The tube 202 also includes a layering fluid 222. The plug 208 may be composed of re-sealable rubber or other suitable re-sealable material that can be repeatedly punctured with a needle or other sharp implement to access the contents of the interior of the tube 202 or to permit introduction of contents into the tube 208 and re-seals when the needle or implement is removed. The plug 208 may be inserted into the tube 202 such that a seal is maintained between the plug 208 and the tube 202, such as by an interference fit. Alternatively, the plug 208 can be formed in the second end of the tube 208 using heated liquid rubber that can be shaped while warm or hot and hardens as the rubber cools. An adhesive may be used to attach the plug 208 to the inner wall of the processing vessel can be a polymer-based adhesive, an epoxy, a contact adhesive or any other suitable material for bonding or creating a thermal bond. Alternatively, the plug 208 may be injected into the tube 202. Alternatively, the plug 208 may be thermally bonded to the tube 202.

The open end of the tube 202 is sized and shaped to receive the cap 100. The shaft 108 of the cap 100 is inserted into the open end of the tube 202, such that the sealing member 110 forms an air-tight seal with an inner wall of the tube 202. The sealing member 110 may be an 0-ring or any appropriate piece which extends circumferentially around the shaft 108 may be used to form the air-tight seal, such as a piece which is compliant, pliable, or stiff. The tube 202 may also include a lip 206 extending at least partially circumferentially around the open end of the tube 202, such that, after insertion and rotation of the cap 100 relative to the tube 202, the lip 206 engages the groove 124 to inhibit longitudinal movement or translation of the cap 100 relative to the tube 202.

The tube 202 may have a tapered geometry that widens or narrows toward the open end; the tube 202 may have a generally cylindrical geometry; or, the tube 202 may have a generally cylindrical geometry in a first segment and a cone-shaped or frusto-conical geometry in a second segment, where the first and second segments are connected and continuous with each other. Although at least one segment of the tube 202 has a circular cross-section, in other embodiments, the at least one segment can have elliptical, square, triangular, rectangular, octagonal, or any other suitable cross-sectional shape. The tube 202 can be composed of a transparent, semitransparent, opaque, or translucent material, such as plastic or another suitable material.

The layering fluid 222 may be miscible or immiscible with the suspension fluid and inert with respect to the suspension materials. The layering fluid 222 may have a density greater than or less than a sample, a target material within the sample, or an analyte within the sample. Examples of suitable layering fluids include, but are not limited to, solution of colloidal silica particles coated with polyvinylpyrrolidone (e.g. Percoll), polysaccharide solution (e.g. Ficoll), iodixanol (e.g. OptiPrep), an organic solvent, a liquid wax, an oil, a gas, and combinations thereof; olive oil, mineral oil, silicone oil, immersion oil, mineral oil, paraffin oil, silicon oil, fluorosilicone, perfluorodecalin, perfluoroperhydrophenanthrene, perfluorooctylbromide, and combinations thereof; organic solvents such as 1,4-Dioxane, acetonitrile, ethyl acetate, tert-butanol, cyclohexanone, methylene chloride, tert-Amyl alcohol, tert-Butyl methyl ether, butyl acetate, hexanol, nitrobenzene, toluene, octanol, octane, propylene carbonate, tetramethylene sulfones, and ionic liquids; polymer-based solutions; surfactants; perfluoroketones, such as perfluorocyclopentanone and perfluorocyclohexanone, fluorinated ketones, hydrofluoroethers, hydrofluorocarbons, perfluorocarbons, perfluoropolyethers, silicon and silicon-based liquids, such as phenylmethyl siloxane; and combinations thereof.

The externality of the pump 212 relative to the tube 202 enhances the ability of the pump 212 to create a pressure gradient, as movement of the pump 212 is not constrained by the internal volume of the tube 202.

Figure 3:
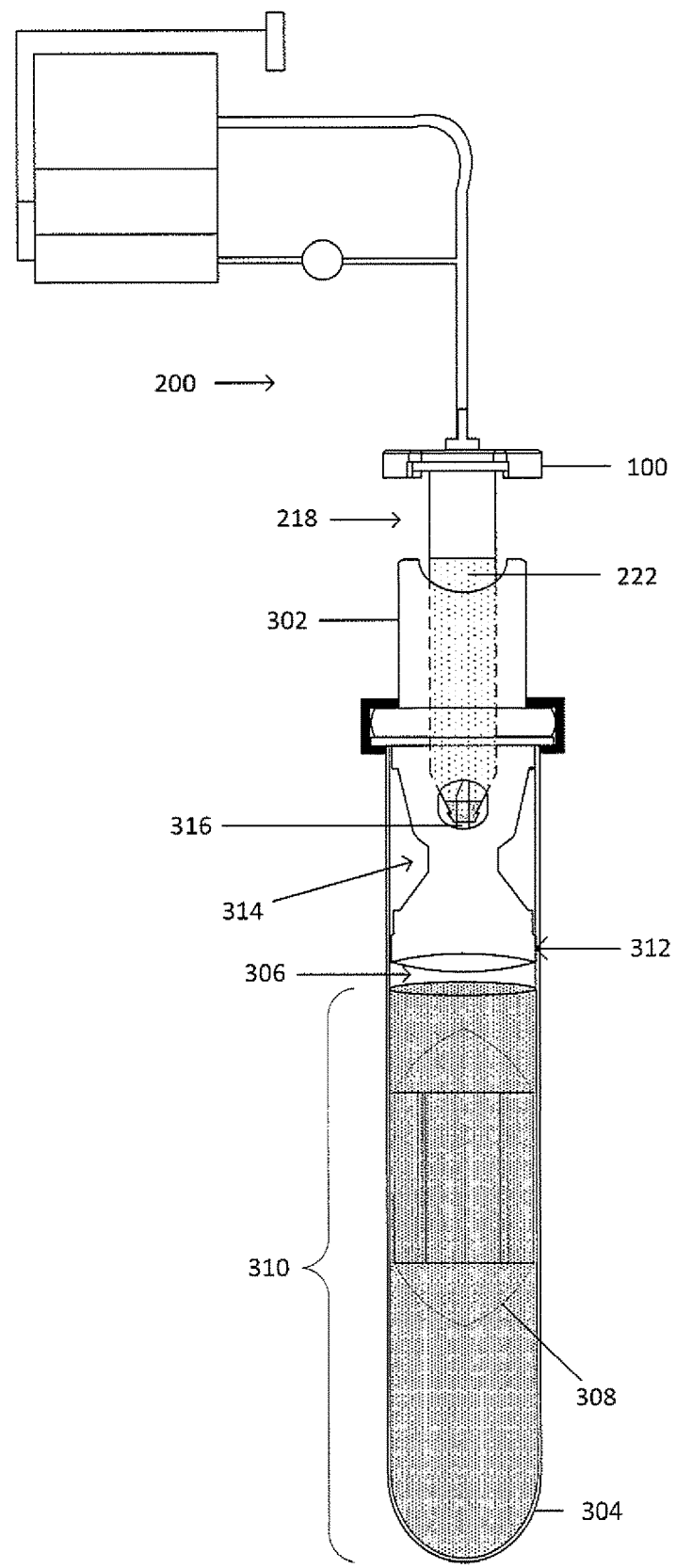
FIG. 3 shows the example fluid layer device connected to a primary vessel.

FIG. 3 shows an isometric view of the fluid layering system 200 connected to a primary vessel 304 by a connector 302. In the example of FIG. 4, the primary vessel 304 has a circular cross-section, a first open end, and a second closed end. The open end is sized to receive a cap 312. The primary vessel may also have two open ends that are sized to receive caps. The primary vessel 304 has a generally cylindrical geometry, but may also have a tapered geometry that widens, narrows, or a combination thereof toward the open end. Although the primary vessel 304 has a circular cross-section, in other embodiments, the primary vessel 304 may have elliptical, square, triangular, rectangular, octagonal, or any other suitable cross-sectional shape that substantially extends the length of the tube. The primary vessel 304 may be composed of a transparent, semitransparent, opaque, or translucent material, such as plastic or another suitable material. The primary vessel 304 includes a central axis and may include a septum at the closed end to permit the removal of a fluid, the suspension, or a suspension fraction, whether with a syringe, a pump, by draining, or the like. The primary vessel 304 may have an inner wall and a first diameter.

The primary vessel 304 includes a sample 310, which may be a solution or a suspension including at least one target analyte or material. For example, the sample 304 may be urine, blood, bone marrow, cystic fluid, ascites fluid, stool, semen, cerebrospinal fluid, synovial fluid, nipple aspirate fluid, saliva, amniotic fluid, vaginal secretions, mucus membrane secretions, aqueous humor, vitreous humor, vomit, a suspension derived from a tissue sample or a culture sample, and any other physiological fluid or semi-solid. It should also be understood that a target material may be a fraction of a sample or a sub-fraction of a fraction, such as a portion of buffy coat. The target material may include an analyte, such as ova, fetal material (e.g. fetal cells, fetal DNA, fetal RNA, fetal red blood cells, fetal white blood cells), endothelial cells, bacteria, viruses (including HIV, cytomegalovirus, hepatitis C virus, Epstein-Barr virus), a vesicle, a liposome, a protein, a nucleic acid, a biological molecule, a naturally occurring or artificially prepared microscopic unit having an enclosed membrane, a microorganism, a cell, a circulating tumor cell, an immune cell, or an inflammatory cell; or, the target material may be the analytes.

The primary vessel 304 may also include a float 308 having a main body, two teardrop-shaped end caps, and support members radially spaced and axially oriented on the main body. Alternatively, the float 308 may not include any support members, such that the primary vessel includes none or at least one support member. Alternatively, the float 308 may include support members which do not engage the inner wall of the primary vessel 304. The float 308 can be composed of a variety of different materials including, but not limited to, metals; organic or inorganic materials; ferrous plastics; sintered metal; machined metal; plastic materials and combinations thereof.

The connector 302, which is inserted into the open end of the primary vessel 304 and includes a cannula 316, such as a needle or tube, fluidly couples the fluid layering system 200 to the primary vessel 304 by puncturing the plug 114 and accessing the contents, such as the layering fluid 222, of the fluid layering system 200 when the fluid layering system 200 is inserted into a cavity within a first end of the connector 302. A second end of the connector 302, being sized and shape to fit within the primary vessel 304, may form an air-tight or fluid-tight seal 312 with an inner wall of the primary vessel 304, thereby forming a sealed portion 306 of the primary vessel 304—extending from the cannula 316, such as the tip of the cannula 316, to the second end of the primary vessel 304—and an unsealed portion of the primary vessel 304. The primary vessel 304, the connector 302, and the tube 218 of the fluid layering system 200 each include their own central axis, such that when the tube 218 of the fluid layering system 200 is inserted into the connector 302 which is inserted into the primary vessel 304, they may all be coaxial with one another.

Upon insertion of the connector 302 into the primary vessel 304 and the fluid layering system 200 into the connector 302, the fluid layering system 200 may be activated, such as by turning the switch 210 to the "on" position. The motor 216 drives the pump 212 thereby creating a pressure gradient between the pump 212 and the sealed portion 306 of the primary vessel 304. Alternatively, the pump 212 may have an internal motor or may not be connected to a motor, where it is desirous to do so, thereby permitting the pump to create the pressure gradient. At least a portion of air trapped within the sealed portion 306 of the primary vessel 304 is drawn through the connector 302 via the cannula 316 and into the fluid layering system 200 via the plug 208 and through the layering fluid 222. The volume of air removed from the sealed portion 306 may be replaced with the layering fluid 222 due to the pressure gradient. The withdrawal of at least a portion of the air within the sealed portion 222 and introduction of the layering fluid 222 is a single cycle. The fluid layering system 200 may undergo any appropriate number of cycles to remove at least a portion of the air from the sealed portion 306 of the primary vessel 304 and replace the removed air with layering fluid 222. For example, the fluid layering system 200 may undergo as many cycles as required, such as up to and including, but not limited to, 10,000 cycles, including, but not limited to, 1, 2, 3, 4, 5, 10, 20, 25, 50, 75, 100, 250, 500, 750, 1000, 2500, 5000, or 7500 cycles. Furthermore, each segment of the cycle may last for any appropriate amount of time to complete the action. For example, each segment may last up to 48 hours, including, but not limited to, 1 millisecond, 10 milliseconds, 100 milliseconds, 1 second, 5 seconds, 10 seconds, 15 seconds, 30 seconds, 60 seconds, 5 minutes, 10 minutes, 15 minutes, 30 minutes, 1 hour, 2 hours, 5 hours, 10 hours, 24 hours, 30 hours, or 36 hours. Additionally, the segments may last the same amount of time or the timing may vary between segments. For example, the withdrawal segment may last 60 seconds and the introduction segment may last 15 seconds. Once a desired or appropriate amount of air from the sealed portion 306 of the primary vessel 304 has been replaced with the layering fluid 222, the switch 106 may be flipped to the "off" position to turn off the motor 216 and/or the pump 212. For example, up to and including 100% of the air from the sealed portion 306 of primary vessel 304, including up to 1%, 5%, 10%, 25%, 33%, 50%, 60%, 66%, 67%, 75%, 80%, 90%, 95%, 99%, and 99.9%, may be removed and replaced with the layering fluid 222.

Alternatively, positive pressure may be used to introduce the layering fluid 222 into the sealed portion 306. Alternatively, pressure feedback, such as by determining the pressure within the tube 218 via the pressure sensor 220, may be used to control (and vary, where appropriate) the pump cycle. For example, a vacuum may be drawn when the pressure sensor 220 denotes a first pressure within the tube 218, a positive pressure may be created when the pressure sensor 220 denotes a second pressure within the tube 218, and the pump 212 may be stopped when the pressure sensor 220 denotes a third pressure within the tube 218. Any appropriate number of cycles may be completed to remove at least a portion of the air from the sealed portion 306 of the primary vessel 304 and replace the removed air with layering fluid 222. During each cycle, the target tube pressures may vary from one vacuum to the next vacuum and from one positive pressure to the next positive pressure. In other words, the vacuum step of different cycles need not be drawn once the pressure sensor 220 reaches the same pressure. The vacuum draw in a first cycle may be performed when the tube 218 reaches a higher or lower pressure than when the vacuum is drawn during the second cycle—and vice versa. For example, drawing the vacuum a first time may occur when the pressure sensor 220 reads +5 psi, whereas drawing the vacuum a second time (after creating the positive pressure a first time) may occur when the pressure sensor 220 reads +3 psi. The same may occur, in terms of different pressure readings, for the positive pressure portion of the cycle Additionally, the two portions of the cycle—withdrawal and introduction—are independent of one another, such that each portion of the cycle may have different flow rates and magnitudes of pressure. The pump 212 may run and/or be controlled differently during the different portions of cycle. For example, withdrawal may be run with the pump creating a pressure different of −14.7 psi, whereas introduction is run with the pump creating a pressure difference of +2-3 psi.

Furthermore, it should be noted that the fluid layering system 200 is self-regulating, such that the fluid layering system 200 does not allow for overfill of the sealed portion 306 of the primary vessel 304. Once the sealed portion 306 of the primary vessel 304 is filled with the layering fluid 222, no more layering fluid 222 may be added due to the absence of any available volume.

The foregoing description, for purposes of explanation, used specific nomenclature to provide a thorough understanding of the disclosure. However, it will be apparent to one skilled in the art that the specific details are not required in order to practice the systems and methods described herein. The foregoing descriptions of specific embodiments are presented by way of examples for purposes of illustration and description. They are not intended to be exhaustive of or to limit this disclosure to the precise forms described. Many modifications and variations are possible in view of the above teachings. The embodiments are shown and described in order to best explain the principles of this disclosure and practical applications, to thereby enable others skilled in the art to best utilize this disclosure and various embodiments with various modifications as are suited to the particular use contemplated.

It is intended that the scope of this disclosure be defined by the following claims and their equivalents:

1. A system comprising:
   a pump;
   a hose comprising a first end and a second end;
   a cap comprising
      a main body comprising a conduit extending in a first direction and a shaft extending in direction opposite the conduit,
      a sealing member extending at least partially around the shaft,
      a cavity extending through the shaft, and
      a bore extending through the conduit and in fluid communication with the cavity; and
   a tube comprising
      a main body comprising a first open end and a second end comprising a plug, and
      a layering fluid,
   wherein the first end of the hose is connected to the pump and the second end of the hose is connected to the conduit of the cap,
   wherein the shaft of the cap is located at least partially within the tube, and
   wherein the sealing member of the cap forms an air-tight seal with an inner wall of the tube.

2. The system of claim 1, further comprising:
   a primary vessel comprising a first open end and a second end; and
   a connector comprising a cavity in a first end, a second end, and cannula extending from the second end at least partially into the cavity and fluidly coupling the first and second ends,
   wherein the second end of the connector is at least partially located within the primary vessel, and
   wherein the cannula extends through the plug of the tube.

3. The system of claim 2, the primary vessel further comprising a sample.

4. The system of claim 3, the layering fluid comprising a density greater than a density of the sample or at least one fraction of the sample.

5. The system of claim 3, the layering fluid comprising a density less than a density of the sample or at least one fraction of the sample.

6. The system of claim 2, wherein the second end of the connector forms an air-tight seal or a fluid-tight seal with an inner wall of the primary vessel.

7. The system of claim 1, wherein the plug is resealable.

8. A method comprising:
   providing a system comprising
      a primary vessel comprising a sample, a first open end, and a second end,
      a pump,
      a hose comprising a first end and a second end,
      a cap comprising a main body comprising a conduit extending in a first direction and a shaft extending in direction opposite the conduit,
a sealing member extending at least partially around the shaft, and
a cavity extending through the shaft, and
a bore extending through the conduit and in fluid communication with the cavity,
a tube comprising
a main body comprising a first open end and a second end comprising a plug, and
a layering fluid, and
a connector comprising a cavity in a first end, a second end, and cannula extending from the second end at least partially into the cavity and fluidly coupling the first and second ends,
wherein the first end of the hose is connected to the pump and the second end of the hose is connected to the conduit of the cap,
wherein the shaft of the cap is located at least partially within the tube,
wherein the sealing member of the cap forms an air-tight seal with an inner wall of the tube, and
wherein the second end of the connector is at least partially located within the primary vessel and forms an air-tight or fluid-tight seal with an inner wall of the primary vessel forming a sealed portion of the primary vessel extending from the cannula to the second end of the primary vessel, and
wherein the cannula extends through the plug of the tube; and
creating a pressure gradient between the pump and the sealed portion of the primary vessel thereby withdrawing at least a portion of the air located within the sealed portion of the primary vessel and replacing the at least a portion of the air with the layering fluid from the tube into the sealed portion of the primary vessel,
wherein the air and the layering fluid are withdrawn and replacing, respectively, through the cannula of the connector.

9. The method of claim 8, wherein the air is withdrawn through the layering fluid within the tube.

10. The method of claim 8, wherein the withdrawing and replacing steps are repeated until at least 50% of the air in the sealed portion of the primary vessel is replaced with the layering fluid.

11. The method of claim 8, wherein the withdrawing and replacing steps are repeated until at least 75% of the air in the sealed portion of the primary vessel is replaced with the layering fluid.

12. The method of claim 8, wherein the withdrawing and replacing steps are repeated until at least 90% of the air in the sealed portion of the primary vessel is replaced with the layering fluid.

13. The method of claim 8, wherein the withdrawing and replacing steps are repeated until at least 99% of the air in the sealed portion of the primary vessel is replaced with the layering fluid.

14. The method of claim 8, wherein the withdrawing and replacing steps are repeated until all of the air in the sealed portion of the primary vessel is replaced with the layering fluid.

15. The method of claim 8, wherein the withdrawing step occurs for up to 60 seconds and the replacing step occurs for up to 15 seconds.

16. The method of claim 8, wherein the withdrawing and replacing steps form a single cycle, and wherein the pump undergoes at least 2 cycles.

17. The method of claim 8, wherein the plug is resealable.

18. The method of claim 8, wherein the withdrawing step occurs for up to 24 hours and the replacing step occurs for up to 24 hours.

19. The method of claim 8, the layering fluid comprising a density greater than a density of the sample or at least one fraction of the sample.

20. The method of claim 8, the layering fluid comprising a density less than a density of the sample or at least one fraction of the sample.

* * * * *